(12) United States Patent
Matthews et al.

(10) Patent No.: US 8,575,147 B2
(45) Date of Patent: Nov. 5, 2013

(54) SPONTANEOUSLY DISPERSIBLE N-BENZOYL STAUROSPORINE COMPOSITIONS

(75) Inventors: Graham Paul Matthews, Horsham (GB); Barbara Haeberlin, Münchenstein (CH)

(73) Assignee: Novartis AG, Basel (CH)

( * ) Notice: Subject to any disclaimer, the term of this patent is extended or adjusted under 35 U.S.C. 154(b) by 169 days.

(21) Appl. No.: 11/859,077

(22) Filed: Sep. 21, 2007

(65) Prior Publication Data

US 2008/0070897 A1 Mar. 20, 2008

Related U.S. Application Data

(63) Continuation of application No. 09/930,335, filed on Aug. 15, 2001, now abandoned, which is a continuation of application No. PCT/EP00/01196, filed on Feb. 14, 2000.

(30) Foreign Application Priority Data

Feb. 16, 1999 (GB) .................................. 9903547.9

(51) Int. Cl.
*A61K 31/553* (2006.01)
*A61P 43/00* (2006.01)

(52) U.S. Cl.
USPC .................................................. 514/211.08

(58) Field of Classification Search
None
See application file for complete search history.

(56) References Cited

U.S. PATENT DOCUMENTS

| | | | |
|---|---|---|---|
| 4,735,939 A | 4/1988 | McCoy et al. | |
| 4,963,367 A | 10/1990 | Ecanow | |
| 5,093,330 A | 3/1992 | Caravatti et al. | |
| 5,444,041 A | 8/1995 | Owen et al. | |
| 5,599,808 A | 2/1997 | Goldstein et al. | |
| 5,639,474 A | 6/1997 | Woo | |
| 5,658,898 A | 8/1997 | Weder et al. | |
| 5,707,648 A | 1/1998 | Yiv | |
| 5,726,164 A | 3/1998 | Weder et al. | |
| 5,736,542 A | 4/1998 | Henry et al. | |
| 5,741,512 A * | 4/1998 | Hauer et al. | 424/450 |
| 5,932,243 A | 8/1999 | Fricker et al. | |
| 5,981,568 A * | 11/1999 | Kunz et al. | 514/411 |
| 6,248,363 B1 * | 6/2001 | Patel et al. | 424/497 |
| 6,306,421 B1 * | 10/2001 | Kunz et al. | 424/423 |
| 6,346,511 B1 | 2/2002 | Singh et al. | |
| 6,472,507 B1 * | 10/2002 | Fischer et al. | 530/326 |
| 6,979,456 B1 * | 12/2005 | Parikh et al. | 424/422 |

FOREIGN PATENT DOCUMENTS

| | | |
|---|---|---|
| AR | 013276 | 12/2000 |
| DE | 44 18 115 | 5/1994 |
| EP | 0 733 358 | 9/1996 |
| EP | 0 657 164 | 6/2005 |
| EP | 0 711 556 | 5/2006 |
| GB | 2257359 | 1/1993 |
| GB | 2 308 545 | 7/1997 |
| WO | WO 95/14037 | 5/1995 |
| WO | WO 9532975 A1 * | 12/1995 |
| WO | WO 96/13273 | 5/1996 |
| WO | WO 98/13032 | 4/1998 |
| WO | WO 98/15255 | 4/1998 |
| WO | WO 98/18321 | 5/1998 |
| WO | WO 98/30204 | 7/1998 |
| WO | WO 98 33512 | 8/1998 |
| WO | WO 99/06024 | 2/1999 |
| WO | WO 99/06043 | 2/1999 |

OTHER PUBLICATIONS

Alken et al. "Effects of a New Protein Kinase C Inhibitor CGP 41251 on T Cell Functions: Inhibition of Activation, Growth, and Target Cell Killing," Cellular Immunology, vol. 150, pp. 137-148 (1993).
Andrejauskas-Buchdunger et al., "Differential Inhibition of the Epidermal Growth Factor, Platelet-derived Growth Factor, and Protein Kinase C-mediated Signal G Transduction Pathways by the Staurosporine Derivative CGP 41251," Cancer Research, vol. 52, pp. 5353-5358 (1992).
Begemann, Martin et al., "Inhibition of the Growth of Glioblastomas by CGP 41251, an Inhibitor of Protein Kinase C, and by a Phorbol Ester Tumor Promoter," Clinical Cancer Research,vol. 2, pp. 1017-1030 (1996).
Begemann, Martin, "Treatment of Human Glioblastoma Cells with the Staurosporine Derivative CGP 41251 Inhibits CDC2 and CDK2 Kinase Activity and Increase Radiation Sensitivity," Anticancer Research, vol. 18,pp. 2275-2282 (1998).
Blobe, Gerard, et al., "Selective Regulation of Expression of Protein Kinase C (PKC) Isoenzymes in Multidrug-resistant MCF-7 Cells," Journal of Biological Chemistry, vol. 268, No. 1, pp. 658-664 (1993).
Caravatti, et al., "Inhibitory Activity and Selectivity of Staurosporine derivatives towards Protein Kinase C," Bioorganic & Medicinal Chemistry Letters, vol. 4, No. 3, pp. 399-404 (1 994).
Chung, Denise et al., "Evidence that the ras oncogene-enclosed p21 protein induces oocyte maturation via activation of protein kinase C," Proc. Natl. Acad. Sci. USA, vol. 89, pp. 1993-1996 (1992).
Dietel, Manfred, "Second International Symposium on Cytostatic Drug Resistance," Cancer Research, vol. 53, pp. 2683-2688 (1993).
Erikson, Raymond L., "Structure, Expression, and Regulation of Protein Kinases Involved in the Phosphorylation of Ribosomal Protein S6," Journal of Biological Chemistry, vol. 266, No. 10, pp. 6007-6010 (1991).
Fuse, E. et al., "Unpredicated Clinical Pharmacology of UCN-01 Caused by Specific Binding to Human alphal-Acid Glycoprotein," Cancer Research, vol. 58, pp. 3248-3253 (1998).
Gottesman, Michael . "How Cancer Cells Evade Chemotherapy: Sixteenth Richard and Hinda Rosenthal Foundation Award Lecture," Cancer Research 53, pp. 747-754 (1993).

(Continued)

*Primary Examiner* — Bong-Sook Baek
(74) *Attorney, Agent, or Firm* — George Dohmann; Matthew Mulkeen

(57) ABSTRACT

Spontaneously dispersible N-benzoyl-staurosporine compositions are discussed for oral administration having high bioavailability levels and reduced variability of bioavailability levels of N-benzoyl-staurosporine, as well as their preparation and use in medical treatment.

12 Claims, 3 Drawing Sheets

(56) References Cited

OTHER PUBLICATIONS

Figure 1:
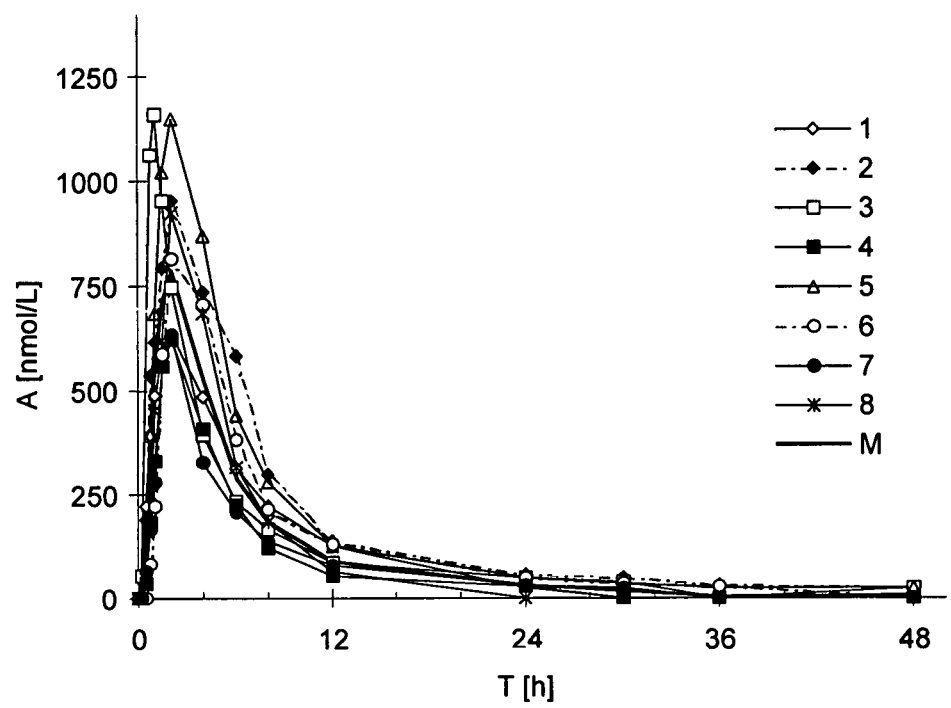

Hilll, D.L., et al.,"Binding of UCN-01 to Plasma Proteins of Humans, Rats and Dogs," Proceeding of the Amer. Assoc. for Cancer Reseaarch, vol. 39, p. 364 (1998).
Ikegam Y. et al., "Effects of the New Selective Protein Kinase C Inhibitor 4'-N-Benzoyl Staurosporine on Cell Cycle Distribution and Growth Inhibition in Human Small Lung Cancer Cells," Jpn. J. Pharmacol. vol. 70, pp. 65-72 (1996).
Ikegami, Yuri et al., "Antitumor Effect of CGP41251, A New Selective Protein Kinase C inhibitor, on Human Non-Small Cell Lung Cancer Cells," Jpn. J. Pharmacol. vol. 70, pp. 65-72 (1996).
Killion J. J. et al., "The Antitumor Activity of Doxorubicin against drug-resistant murine carcinoma is enhanced by oral administration of synthetic staurosporine analogue," Oncology Research, vol. 7, No. 9, pp. 453-459 (1995).
Ludescher Ch et al., "Decreased Potency of MDR-modulators under serum conditions determined by a functional assay," Brit. J. of Haematology,vol. 91, pp. 652-657 (1995).
Mack, P.C. et al. "7-hydroxystaurosporine (UCN-01) plus cisplatin (CDPP): molecular mechanism of dose-, time- and sequence-dependent potentiation in non-small cell lung carcinoma (NSCLC)," Clinical Pharmacology, Proceeding of Asco.vol. 16, pp. 212a.
Matte, B.M. et al. "Protein Kinase C and Mammary Cell Differentiation: Involvement of Protein Kinase C alpha in the Induction of Beta-Casein Expression," Cell Growth & Differentiation, vol. 5, pp. 239-247 (1994).
Matter A., et al., "Pharmacological Approach to growth regulation of breast cancer cells," In: M.E. Lippman and E. Mihich, Editors, The therapeutic implications of the molecular biology of breast cancer, Pezcoller Foundation Symposia, John Libbey CIC, Trento, Italy (1990), pp. 227-246.
Meggio, Flavio, et al., "Different susceptibility of protein kinases to staurosporine inhibition," Eur. J. Biochem. vol. 234, pp. 317-322 (1995).
Meyer, Th. et al. "A Derivative of Staurosporine (CGP 41251) Shows Selectivity for Protein Kinse C Inhibition and In Vitro Anti-proliferative as well as In Vivo Anti-tumor Activity," Int. J. Cancer, vol. 43, pp. 851-856 (1989).
Miyamoto, Ken-ichi, "Inhibition of Multidrug Resistance by a New Staurosporine Derivative, NA-382, in Vitro and in Vivo," Cancer Resarch, vol. 53,pp. 1555-1559 (Apr. 1, 1993).
Pastan et al.,"Multidrug Resistance," Annu. Rev. Med., vol. 42, pp. 277-86 (1991).
Sampson, K. E. et al., "Staurosporine reduces P-glycoprotein expression and modulates multidrug resistance," Cancer Letters, vol. 68, pp. 7-14 (1993).
Sato, Walkao et al., "Staurosporine, a potent inhibitor of C-kinase enhances drug accumulation in multidrug-resistant cells," Biochemical and Biophysical Research Communications, vol. 173, No. 3, pp. 1252-1257 (1990).
Sedlak, J. et al., "Effects of protein kinase C inhibitor, staurosporine derivative CGP 41251, on cell cycle, DNA synthesis and Drug uptake in neoplastic cell lines," Anti-Cancer Drugs, vol. 6, pp. 70-76 (1995).
Simon, Sanford et al., "Cell biological mechanisms of multidrug resistance in tumors," Proc. Natl. Acad. Sci, USA, vol. 91, pp. 3497-3504 (1994).
Susa, Mira et al., "Inhibition or Down-regulation of Protein Kinase C Attenuates Late Phase p70s6k Activation Induced by Epidermal Growth Factor but Not by Platelet-derived Growth Factor or Insulin," Journal of Biological Chemistry, vol. 267, No. 10, pp. 6905-6909 (1992).
Utz I. et al., "The Protein Kinase C Inhibitor CGP 41251, A Staurosporine Derivative with Antitumor Activity, Reverses Multidrug Resistance," Int. J. Cancer, vol. 57, pp. 104-110 (1994).
Utz, I., "Reversal of Multridrug Resistance by the Staurosporine Derivatives CGP 41251 and CGP 42700," Int. J. Cancer, vol. 77, pp. 64-69 (1998).
Van Kalken et al., "Multidrug Resistance from the Clinical Point of View," Eur. J.Cancer, vol. 27, No. 11, pp. 1461-1486 (1991).
Schwarz, et al. "Effect on the partition equilibrium of various drugs by the formation of mixed bile salt/phosphatidylcholine/fatty acid micelles a characterization by micellar affinity capillary electrophoresis Part IV," Journal of Chromatography A, vol. 809, pp. 219-229 (1998).
Borkovec, Michal, "Phenommenologial theories of Globular Microemulsion," Advances in Colloid and Interface Science., vol. 37, pp. 195-217 (1992).
Beltran, Pedro et al., "Chemosensitization of Cancer Cells by the Staurosporine Derivative CGP 41251 in Association with Decreased P-Glycoprotein Phosphorylation," Biochemial Pharmacology, vol. 53, pp. 245-247 (1997).
Ikegami Y., Arzneim.-Forsch./Drug Res. 46 (I), No. 2 1996, p. 201-204.
Bachynsky et al., "Factors Affecting the Efficiency of a Self-Emuslifying Oral Delivery System", Drug Development and Industrial Pharmacy, 1997, vol. 23, No. 8, pp. 809-816.

\* cited by examiner

SPONTANEOUSLY DISPERSIBLE N-BENZOYL STAUROSPORINE COMPOSITIONS

This application is a continuation of U.S. application Ser. No. 09/930,335, filed Aug. 15, 2001, which is a continuation of International Application No. PCT/EP00/01196, filed Feb. 14, 2000.

The present invention relates to novel pharmaceutical compositions in which an active agent is N-benzoyl-staurosporine as disclosed e.g. in U.S. Pat. No. 5,093,330 and equivalents thereof.

U.S. Pat. No. 5,093,330 specifically discloses two tablet formulations based on starch/lactose mixtures in the presence of colloidal silica, talc and magnesium stearate (Examples 52 and 53) and a capsule formulation based on talc and colloidal silica (Example 54). We have found that N-benzoyl-staurosporine presents highly specific difficulties in relation to administration generally and pharmaceutical compositions in particular, including problems with drug bioavailability and variability in inter- and intra-patient dose response, e.g. with respect to U.S. Pat. No. 5,093,330. We have found it to be very lipophilic and practically insoluble in water, in simulated gastric and in intestinal fluids (solubility<0.1 mg/L). In particular this exceptional low solubility of the active substance necessitated development of a non-conventional dosage form.

In accordance with the present invention it has now surprisingly been found that stable pharmaceutical compositions with N-benzoyl-staurosporine having particularly interesting bioavailability characteristics and reduced variability in inter- and intra-subject bioavailability parameters, e.g. with respect to U.S. Pat. No. 5,093,330, are obtainable. These novel N-benzoyl-staurosporine compositions have been found to meet or substantially reduce the difficulties encountered previously. It has been shown that the compositions in accordance with the present invention may enable effective N-benzoyl-staurosporine dosaging with concomitant enhancement as well as reduced variability of resorption/bioavailability levels for and between individual patients. Such reductions in variability in in inter- and intra-subject bioavailability may be particularly found with respect to the specific formulations described. More particularly, it has been found that these compositions may contain solubilized N-benzoyl-staurosporine in sufficiently high concentration to permit convenient oral administration without exhibiting precipitation of the active agent. Thus, the invention may achieve effective therapy with lower N-benzoyl-staurosporine dosage levels and may permit closer standardization and optimization of daily dosage requirements for each individual. Consequently, occurrence of undesirable side-effects is diminished and overall cost of therapy may be reduced.

BRIEF DESCRIPTION OF THE DRAWINGS

FIG. 1 shows plasma concentrations of N-benzoyl-staurosporins in dogs after oral administration of single dose of 50 mg of formulation A.

FIG. 2 shows plasma concentrations of N-benzoyl-staurosporins in dogs after oral administration of single dose of 50 mg of formulation A.

FIG. 3 shows plasma concentrations of N-benzoyl-staurosporins in dogs after oral administration of single dose of 50 mg of formulation A.

In one aspect the present invention provides a pharmaceutical composition for oral administration comprising N-benzoylstaurosporine having a high level of bioavailability, e.g.

as determined by measuring plasma concentrations over time, as defined by the Area Under the Curve (AUC) in units of mass-time/volume.

In another aspect the present invention provides a pharmaceutical composition for oral administration comprising N-benzoylstaurosporine having a reduced variability of bioavailability. In preferred embodiments variability of bioavailability is reduced by providing N-benzoylstaurosporine in form of a spontaneously dispersible pharmaceutical composition.

In another aspect the present invention provides a spontaneously dispersible pharmaceutical composition for enteral, e.g. oral, administration comprising N-benzoyl-staurosporine, for example in the form of a micellar precursor.

The term spontaneously dispersible pharmaceutical composition as used herein is defined as a system that is capable of producing colloidal structures, e.g. colloids or analogous structures, e.g. droplets, particles, micelles, e.g. swollen micelles, microemulsions and/or aggregates, of e.g. up to 1000 nm, e.g. generally more than 5 nm, when diluted with an aqueous medium. Such systems may be defined as consisting of one component or phase (the dispersed component or phase) finely divided and distributed throughout a second component or phase (the dispersion medium or contiuous component or phase), e.g. systems ranging from molecularly dispersed solutions wherein the mean size of the dispersed component or phase may be e.g. less than 200 nm, e.g. more than 5 nm, to macroemulsions wherein the mean size of the dispersed component or phase may be of e.g. up to 1000 nm, e.g. more than 200 nm. The aqueous medium may be for example water, for example on dilution of e.g. 1:10, or gastric juices, e.g. simulated conditions after oral application. The colloidal structures, e.g. colloids or analogous structures, e.g. droplets, particles and/or micelles, are formed spontaneously or substantially spontaneously when the components of the dispersible pharmaceutical composition are brought into contact with an aqueous medium, e.g. by simple shaking by hand for a short period of time, for example for 10 seconds. Such spontaneously dispersible pharmaceutical compositions are thermodynamically stable, e.g. from at least 15 minutes or 4 hours to 24 hours. Typically, they contain dispersed, e.g. colloidal structures, e.g. colloids or analogous structures, of a size less than about 200 nm as measured by standard light scattering techniques, e.g. using a Malvern Zetasizer 3000, preferably they comprise droplets or particles having a mean diameter of less than about 150 nm, typically less than 100 nm, generally greater than 5 nm. The micellar compositions or the micellar part of such spontaneously dispersible compositions may be monophasic and substantially non-opaque, i.e. transparent or opalescent when viewed by optical microscopic means.

Alternatively, the spontaneously dispersible pharmaceutical composition may form simultaneously a mixture comprising aqueous micelles and nanoparticles. Such nanoparticles may have a particle size of from 150 nm to about 1000 nm, generally in the range of 200 to 800 nm. It was found that the amount of nanoparticles produced may be temperature dependent but still adequate bioavailability characteristics may be obtained.

Although the invention has been described particularly with respect to a spontaneously dispersible pharmaceutical composition a man skilled in the art will appreciate that other systems may be prepared.

In another aspect the present invention provides a spontaneously dispersible pharmaceutical composition for oral administration comprising 1) N-benzoyl-staurosporine,
2) a hydrophilic component, and
3) a surfactant.

In yet another aspect the invention provides a method of increasing bioavailability of N-benzoylstaurosporine by mixing N-benzoylstaurosporine with a carrier comprising a hydrophilic component, and a surfactant.

In another aspect the present invention provides a pharmaceutical composition for increasing the bioavailability of N-benzoylstaurosporine which comprises
1) N-benzoyl-staurosporine,
2) a hydrophilic component, and
2) a surfactant.

The spontaneously dispersible pharmaceutical composition (hereinafter embraced by the term pharmaceutical composition of the present invention) is preferably in the form of a colloidal structures, e.g. colloids or analogous structures, e.g. a micellar precursor. N-benzoyl-staurosporine is hereinafter also referred to as the active agent and all other components of the spontaneously dispersible pharmaceutical composition may be hereinafter referred to as the carrier of the spontaneously dispersible pharmaceutical composition. The components of the spontaneously dispersible pharmaceutical compositions may be described in Fiedler, H. P. "Lexikon der Hilfsstoffe für Pharmazie, Kosmetik und angrenzende Gebiete", Editio. Cantor, D-7960 Aulendorf, 4th revised and expanded edition (1996), the contents of which are hereby incorporated by reference.

In accordance with the present invention N-benzoyl-staurosporine may be present in an amount by weight of up to about 20% by weight of the composition. Preferably the active agent is present in an amount of 1 to 15% by weight of the composition, for example about 5 to 10%, and more preferred 5%.

The hydrophilic component preferably provides for fast mixing of the active agent with water on admixture with water and may be determined by routine experimentation, for example by various chromatography methods, e.g. Gas Chromatography (GC). The hydrophilic component may comprise a main or sole component, e.g. an alcohol, e.g. ethanol, or alternatively may comprise a co-component which may be selected from partial ethers or lower alkanols. Preferred lower alkanol components include ethanol, 1,2-propylene glycol or a polyethylene glycol, e.g. of a molecular weight of 100 to 600 daltons, e.g. polyethylene glycol 400. When present in the invention ethanol may comprise up to 60% by weight of the hydrophilic component; preferably 20 to about 55% by weight, more preferably about 25 to about 40% by weight. Especially preferred partial ethers are those known and commercially available as for example glycofurol (also known as tetrahydrofurfuryl alcohol polyethylene glycol ether). These co-components when present are e.g. a partial replacement of other components of the hydrophilic component such that the efficacy of the hydrophilic component as part of the N-benzoyl-staurosporine carrier is not materially impaired. The hydrophilic component may further comprise triethylcitrate, Transcutol, N-methylpyrrolidone, dimethylisosorbide, or propylene carbonate.

The total amount of the hydrophilic component present in the spontaneously dispersible pharmaceutical compositions of the present invention may comprise 5 to 50% by weight of the carrier, e.g. 10 to 50%; preferably 10 to 40% by weight, more preferably about 15 to 35% by weight.

Pharmaceutical compositions of the present invention further comprise at least one pharmaceutically acceptable surfactant. Surfactants useful for the present invention may be of the anionic, cationic, amphoteric or non-ionic type or mixtures thereof and have generally a hydrophilic-lipophilic balance (HLB) value of from about 3 to 20. Usually nonionic surfactants are preferred, particularly those non-ionic surfactants that have an HLB value of greater than 10, e.g. 14 to 20. Alternatively, the pharmaceutical compositions of the present invention may embrace systems comprising a mixture of surfactants, e.g. a mixture of a first surfactant and one or more co-surfactants selected from any of the surfactant types listed below. Especially preferred are specific combinations of a surfactant having a high HLB value with a co-surfactant having a low HLB value, for example a combination of a polyoxyethylene castor oil derivative, e.g. Cremophor RH 40 (HLB 14-16) and a transesterified ethoxylated vegetable oil, e.g. Labrafil M2125 CS (HLB 3-4).

Particularly preferred surfactants of high HLB value, e.g. HLB>10, are the following:

(i) Reaction products of a natural or hydrogenated vegetable oil and ethylene oxide, i.e. polyoxyethylene glycolated natural or hydrogenated vegetable oils, for example polyoxyethylene glycolated natural or hydrogenated castor oils. The natural or hydrogenated castor oil may be reacted with ethylene oxide in a molar ratio of from about 1:35 to about 1:60, with optional removal of the polyethyleneglycol component from the products. Various of such surfactants are commercially available. The polyethyleneglycol hydrogenated castor oils available under the trade name CREMOPHOR are especially suitable (Fiedler, loc. cit., 1, p. 392-395). Particularly suitable are CREMOPHOR. RH 40, which has a saponification number of about 50 to 60, an acid number less than about 1, a water content (Fischer) less than about 2%, an $n_D^{60}$ of about 1.453 to 1.457 and an HLB of about 14 to 16; and CREMOPHOR RH 60, which has a saponification number of about 40 to 50, an acid number less than about 1, an iodine number of less than about 1, a water content (Fischer) of about 4.5 to 5.5%, an $n_D^{25}$ of about 1.453 to 1.457 and an HLB of about 15 to 17. An especially preferred product of this class is CREMOPHOR RH40. Also suitable are polyethyleneglycol castor oils such as that available under the trade name CREMOPHOR EL, which has a molecular weight (by steam osmometry) of about 1630, a saponification number of about 65 to 70, an acid number of about 2, an iodine number of about 28 to 32 and an $n_D^{25}$ of about 1.471 and an HLB value of about 12 to 14. Also suitable are the various tensides available under the trade names NIKKOL (e.g. NIKKOL HCO-40 and HCO-60), MAPEG (e.g. MAPEG CO-40h), INCROCAS (e.g. INCROCAS 40), and TAGAT, for example polyoxyethylene-glycerol-fatty acid esters, e.g. TAGAT RH 40, and polyoxyethylene-glycerol-trioleates, e.g. TAGAT TO having a HLB value of 11.3. These surfactants are further described in Fiedler loc. cit.

(ii) Related products that belong to the class of polyoxyethylene alkyl ethers are available under the tradename BRIJ, e.g. Brij 35 which has an HLB value of about 16.9.

(iii) Polyoxyethylene fatty acid esters, for example polyoxyethylene stearic acid esters of the type known and commercially available under the trade name MYRJ (Fiedler, loc. cit., 2, p. 1042-1043). An especially preferred product of this class is MYRJ 52 having a $n_D^{25}$ of about 1.1, a melting point of about 40 to 44° C., an HLB value of about 16.9, an acid value of about 0 to 1 and a saponification no. of about 25 to 35. Other related products include polyethoxylated saturated hydroxy fatty acids which may be produced by reacting a saturated hydroxy fatty acid, e.g. $C_{18}$ to $C_{20}$ with e.g. ethylene oxide or polyethylene glycol. Suitable examples for the present invention include are known and commercially available, e.g. from the BASF company under the trade mark Solutol. Especially preferred is Solutol HS15 which is known, e.g. from the BASF technical leaflet MEF 151E (1986), to comprise of about 70% polyethoxylated 12-hydroxystearate by weight and about 30% by weight unesterified polyethylene glycol component. Solutol HS 15 has a hydrogenation value of 90 to 110, a saponification value of 53 to 63, an acid number of maximum 1, and a maximum water content of 0.5% by weight.

(iv) Polyoxyethylene-sorbitan-fatty acid esters (also called polysorbates), for example mono- and tri-lauryl, palmityl, stearyl and oleyl esters of the type known and commercially available under the trade name TWEEN (Fiedler, loc. cit., 2, p. 1615-1619) including the products TWEEN.
20 [polyoxyethylene(20)sorbitanmonolaurate] with an HLB of about 16.7,
21 [polyoxyethylene(4)sorbitanmonolaurate] with an HLB of about 13.3,
40 [polyoxyethylene(20)sorbitanmonopalmitate] with an HLB of about 15.6,
60 [polyoxyethylene(20)sorbitanmonostearate] with an HLB of about 14.9,
65 [polyoxyethylene(20)sorbitantristearate] with an HLB of about 10.5,
80 [polyoxyethylene(20)sorbitanmonooleate] with an HLB of about 15.0,
81 [polyoxyethylene(5)sorbitanmonooleate] with an HLB of about 10.0,
85 [polyoxyethylene(20)sorbitantrioleate] with an HLB of about 11.0.
Especially preferred products of this class are TWEEN 40 and TWEEN 80.

(v) Hydrophilic tocopherol esters, e.g. d-alpha-tocopheryl polyethylene glycol 1000 succinate.

(vi) Polyoxyethylene-polyoxypropylene co-polymers and block co-polymers, for example of the type known and commercially available under the trade names PLURONIC, EMKALYX and POLOXAMER (Fiedler, loc. cit., 2, p. 1198-1204). An especially preferred product of this class is PLURONIC F68, having a melting point of about 52° C. and a molecular weight of about 6800 to 8975. A further preferred product of this class is POLOXAMER 188, which has an HLB value of about 29.

Particularly preferred co-surfactants having a low HLB value, e.g. HLB<10, are the following:
(i) Sorbitan fatty acid esters, e.g. of the type known and commercially available under the trade name Span, for example including sorbitan-monolaureyl ester (HLB 8.6), -monopalmityl ester (HLB 6.7), -monostearyl ester (HLB 4.7), -tristearyl ester (HLB 2.1), -monooleyl ester (HLB 4.3), and -trioleyl esters (HLB 1.8) (Fiedler, loc. cit., 2, p. 1430).
(ii) Propylene glycol mono- and di-fatty acid esters such as propylene glycol dicaprylate (also known and commercially available under the trade name MIGLYOL 840), propylene glycol dilaurate, propylene glycol hydroxystearate, propylene glycol isostearate, propylene glycol laurate, propylene glycol ricinoleate, propylene glycol stearate and so forth (Fiedler, loc. cit., 2, p. 1008-1010). Propylene glycol mono $C_8$ esters include Sefsol 218 (Nikko Chemicals) and Capryol 90 (Gattefossè).

(iii) Transesterified ethoxylated vegetable oils such as those obtained by reacting various natural vegetable oils (for example, maize oil, kernel oil, almond oil, ground nut oil, olive oil, soybean oil, sunflower oil, safflower oil and palm oil, or mixtures thereof) with polyethylene glycols that have an average molecular weight of from 200 to 800, in the presence of an appropriate catalyst (according to known procedures described in the literature, e.g. U.S. Pat. No. 3,288,824). Transesterified ethoxylated corn oil is particularly preferred. Various forms of transesterified ethoxylated vegetable oils are known and commercially available under the trade name LABRAFIL (Fiedler, loc cit, 2, p. 880). Especially suitable examples are LABRAFIL M 2125 CS (obtained from corn oil and having an acid number of less than about 2, a saponification number of 155 to 175, an HLB value of 3 to 4, and an iodine number of 90 to 110), and LABRAFIL M 1944 CS (obtained from kernel oil and having an acid number of about 2, a saponification number of 145 to 175 and an iodine number of 60 to 90). LABRAFIL M 2130 CS (which is a transesterification product of a $C_{12-18}$ glyceride and polyethylene glycol and which has a melting point of about 35 to 40° C., an acid number of less than about 2, a saponification number of 185 to 200 and an iodine number of less than about 3) may also be used. The preferred transesterified ethoxylated vegetable oil is LABRAFIL M 2125 CS which can be obtained, for example, from Gattefossè, Saint-Priest Cedex, France.

(iv) Mono-, di- and mono/diglycerides, e.g. $C_8$ to $C_{10}$ fatty acid mono- and di-glycerides include Capmul MCM, Akoline MCM (from the Karlshamns company), Imwitor 308 and Imwitor 988, which have an HLB value of about 3.8 (from the Contensio company), and especially esterification products of caprylic or capric acid with glycerol. Preferred products are of this class are e.g. those comprising or essentially consisting of caprylic/capric acid mono- and di-glycerides. $C_8$ to $C_{10}$ mono-, di-glycerides having 6 to 10 mol-% polyoxyethylene groups, e.g. Softigen 767 (available from Contensio Chemicals). Monoglycerides, e.g. monooleate, glycerol monopalmitate and glycerol monostearate, for example as known and commercially available under the trade names Myvatex, Myvaplex, and Myverol (Fiedler, loc. cit., 2 p. 1044) and acetylated, e.g. mono- and di-acetylated monoglycerides, for example as known under the trade name Myvacet (Fiedler, loc. cit., 2, p. 1043).

(v) Pentaerythriol fatty acid esters and polyalkylene glycol ethers and polyalkylene glycol ethers, for example pentaerythrite-dioleate, -distearate, -monolaurate, -polyglycol ether, and -monostearate as well as pentaerythrite-fatty acid esters (Fiedler, loc. cit., 2, p. 1158-1160)

(vi) Other suitable surfactants include glycerol triacetate or (1,2,3)-triacetin (Fiedler, loc. cit., 2, p. 1580); and sterols and derivatives thereof.

Further ionic surfactant classes not represented by the categories described above include
(i) Docusate salts, for example dioctylsulfosuccinate or related compounds, for example di-[2-ethylhexyl]-succinate (Fiedler, loc. cit., 1, p. 500).
(ii) Phospholipids, in particular lecithins (Fiedler, loc. cit., 2, p. 910-912). Lecithins suitable for use in the compositions of the invention include, in particular, soya bean lecithins.

Thus, in another aspect the present invention provides a spontaneously dispersible pharmaceutical composition for oral administration comprising N-benzoyl-staurosporine and a surfactant selected from the group consisting of polyoxyethylenes, for example a polyoxyethylene castor oil, e.g. Cremophor RH40, a polyoxyethylene alkyl ether, e.g. Brij 35, polyglycerols and related polyols, for example a polysorbate, e.g. Tween 20, and polyalkylene oxide copolymers, e.g. Pluronic.

Furthermore, in yet another aspect the present invention provides a spontaneously dispersible pharmaceutical composition for oral administration comprising N-benzoyl-staurosporine and a surfactant having a high HLB value of greater than 10, for example selected form the group consisting of a polyoxyethylene castor oil, e.g. Cremophor RH 40, a polyoxyethylene alkyl ether, e.g. Brij 35, and a polysorbate, e.g. Tween 20, and co-surfactant having a low HLB value of less than 10, for example a transesterified ethoxylated vegetable oil, e.g. Labrafil M2125 CS.

Such spontaneously dispersible pharmaceutical composition may be formulated in a conventional manner and may preferably be in a form of a micellar precursor as described above.

The total amount of surfactant and co-surfactant present in the pharmaceutical composition of the present invention may comprise 5 to 80% by weight of the carrier; preferably 10 to 70% by weight, more preferably 20 to 60% by weight and even more preferably between about 30% and 55% by weight.

The pharmaceutical compositions of the present invention may further comprise a lipophilic component. These compositions may be capable of producing emulsions and related systems, e.g. microemulsions, e.g. a system with a mean particle diameter of e.g. from 5 nm to 200 nm, e.g. from 5 nm to 100 nm, e.g. aqueous or oily microemulsions, preferably an aqueous microemulsion, upon mixing with an aqueous medium. Preferably the lipophilic component may be characterized by a low HLB value of less than 10, e.g. up to 8. The lipophilic component may comprise fatty acid triglycerides, preferably medium chain fatty acid triglycerides. Especially suitable medium chain fatty acid triglycerides are neutral oils, e.g. neutral plant oils, in particular fractionated coconut oils, for example those known and commercially available under the trade names Captex, Myritol, Capmul, Neobee and Mazol; Miglyol 812 being the most preferred. Miglyol 812 is a fractionated coconut oil comprising caprylic-capric acid triglycerides and having a molecular weight=about 520 daltons. Fatty acid composition=$C_6$ max. about 3%, $C_8$ about 50 to 65%, $C_{10}$ about 30 to 45%, $C_{12}$ max 5%; acid no.=about 0.1; saponification no. about 330 to 345; iodine no.=max 1. Miglyol 812 is available from the Hüls company. Other suitable triglycerides preferably comprise mixtures of $C_{8-10}$ or $C_{12-20}$ fatty acid triglycerides, especially $C_{16-18}$ fatty acid triglycerides. The fatty acid component of the triglycerides may comprise both saturated and unsaturated fatty acid residues. Preferably however they are predominantly comprised of unsaturated fatty acid residues; in particular $C_{18}$ unsaturated fatty acid residues. Suitably the triglycerides comprise at least 60%, preferably at least 75%, more preferably at least 85% by weight of a $C_{18}$ unsaturated fatty acid (for example linolenic, linoleic and oleic acid) triglycerides. Suitably the triglycerides comprise less than 20%, for example about 15% or 10% by weight or less, saturated fatty acid (for example palmitic and stearic acid) triglycerides.

The lipophilic component may also comprise a transesterification product, generally obtained as described in GB 2 257 359 or WO 94/09211, the contents of which are incorporated herein by reference. Other particularly suitable triglycerides are the purified transesterification products of corn oil and glycerol, hereinafter referred to as corn oil glycerides and produced according to the description of GB 2 257 359 or WO 94/09211.

Thus, in another aspect, the invention provides a spontaneously dispersible pharmaceutical composition for oral administration comprising N-benzoyl-staurosporine and a surfactant having a HLB value of greater than 10 and a fatty acid glyceride as a lipophilic component.

The total amount of lipophilic component when present in the spontaneously dispersible pharmaceutical compositions may comprise 5 to 85% by weight of the carrier, e.g. 10 to 85%; preferably 15 to 70% by weight, more preferably about 20 to about 50% by weight.

Accordingly, in yet another aspect the present invention provides a spontaneously dispersible pharmaceutical composition for oral administration comprising N-benzoyl-staurosporine, a surfactant selected from the group consisting of a polyoxyethylene castor oil, e.g. Cremophor RH 40, a polyoxyethylene alkyl ether, e.g. Brij 35, and a polysorbate, e.g. Tween 20, and a lipophilic component selected from the group consisting of a fatty acid glycerides, for example a fractionated coconut oil, e.g. Miglyol 810 and 812, a corn oil glyceride, and a acetylated mono- or diglyceride, respectively.

Such spontaneously dispersible pharmaceutical composition may be formulated in a conventional manner and may preferably be in a form of a micellar precursor as described above.

Where desired, the pharmaceutical compositions of the present invention may comprise further additives or ingredients, for example thickening agents, suspending agents, solidifying agents, as well as antioxidants, e.g. tocopherols, ascorbyl palmitate, butyl hydroxy anisole (BHA), butyl hydroxy toluene (BHT), antimicrobial agents, enzyme inhibitors, stabilizers, preserving agents, and the like. The total amount of these additives or ingredients when present in the invention may comprise about 0.05 to 5%, preferably 0.1 to 1%, by weight of the total weight of the spontaneously dispersible pharmaceutical composition. The spontaneously dispersible pharmaceutical composition may also include sweetening or flavoring agents in an amount of up to about 2.5 or 5% by weight based on the total weight of the composition.

Thus in yet another aspect, the present invention provides a spontaneously dispersible pharmaceutical composition for oral administration comprising (a) up to 20% by weight of N-benzoyl-staurosporine,
(b) 5 to 50% by weight of a hydrophilic component,
(c) 5 to 80% by weight of a surfactant or surfactant mixture,
(d) 5 to 85% by weight of a lipophilic component, and
(e) 0.05 to 5% by weight of an additive.

Naturally, any pharmaceutical composition of the present invention as described above in form of a micellar precursor can itself, i.e. before dilution with an aqueous medium, or after dilution with an aqueous medium, be present in the form of a an aqueous micellar solution (possibly comprising nanoparticles), an oily or aqueous emulsion, preferably a microemulsion, and accordingly exhibit the structural features characteristic of such systems.

The pharmaceutical formulations, e.g. those in the examples hereinafter, may show good stability characteristics as indicated by standard stability trials, for example having a shelf life stability of up to one, two or three years, and even longer. The pharmaceutical formulations of this invention produce aqueous microemulsions or aqueous micelles which are stable for up to one day or longer.

The pharmaceutical compositions of the invention exhibit especially advantageous properties when administered orally. For example in terms of reduced variability and high level of bioavailability, e.g. obtained in standard bioavailability trials, e.g. by measuring the area under the plasma concentration(AUC)-time curve from e.g. 0 to 48 h, in units of mass-time/volume and $C_{max}$ average, defined as highest observed concentration in plasma in units mass/volume. Such biopharmaceutical properties of the compositions of the invention, e.g. the compositions of the Examples, may be determined in conventional manner, e.g. in standard animal tests, e.g. in rats or dogs, e.g. beagle dogs, or clinical trials. Typically, fasted beagle dogs, e.g. in groups of up to 8, e.g. 6 to 8, may be used and blood drug levels detected, e.g. using an HPLC method with fluorescence detection or e.g. by ELISA using a specific monoclonal antibody. Typically a dose of e.g. 25 mg or 50 mg, e.g. 50 mg, of active agent may be administered. For example, typical AUC/dose values in (h·nmol/L)/(mg/kg) range from 960 to 1700 for Formulation A, from 380 to 1760 for Formulation B, and from 840 to 1970 for Formulation C. Typical $C_{max}$/dose values in (nmol/L)/(mg/kg) range from 130 to 310 for Formulation A, from 60 to 280 for Formulation B, and from 140 to 310 for Formulation C.

In one aspect the invention provides a pharmaceutical composition for oral administration comprising N-benzoylstaurosporine having an AUC(0-48 h)/dose value (in (h·nmol/L)/(mg/kg)) upon administration of a dose (in mg/kg) to fasted beagle dogs of up to 2000, e.g. from 380 to 2000, e.g. from 840 to 2000.

In another aspect the invention provides a pharmaceutical composition for oral administration comprising N-benzoyl-staurosporine having a $C_{max}$/dose value (in (nmol/L)/(mg/kg)) upon administration of a dose (in mg/kg) to fasted beagle dogs of up to 310, e.g. from 60 to 310, e.g. from 140 to 310.

Pharmacokinetic parameters, for example absorption and blood levels, also become surprisingly more predictable and problems in administration with erratic absorption may be eliminated or reduced. It has been found that the compositions of this invention reduce variability in inter- and intra-patient dose response. Typically, the variabilty of bioavailability is about 10% for Formulation A, about 17% for Formulation B, and about 14% for Formulation C.

In another aspect the invention provides a pharmaceutical composition for oral administration comprising N-benzoyl-staurosporine and having a variability of bioavailability of N-benzoylstaurosporine of less than 20%, e.g. from 5% to 17%, e.g. from 10% to 17%.

In another aspect the invention provides a method of increasing bioavailability or reducing variability of bioavailability levels of N-benzoylstaurosporine, said method comprising orally administering a composition of the invention to fasted beagle dogs, e.g. wherein N-benzoylstaurosporine has an AUC(0-48 h)/dose value (in (h·nmol/L)/(mg/kg)) upon administration of a dose (in mg/kg) to fasted beagle dogs of up to 2000, e.g. from 380 to 2000, e.g. from 840 to 2000.

In another aspect the invention provides a method of increasing bioavailability or reducing variability of bioavailability levels of N-benzoylstaurosporine, said method comprising orally administering a composition of the invention to fasted beagle dogs, e.g. wherein N-benzoylstaurosporine has a $C_{max}$/dose value (in (nmol/L)/(mg/kg)) upon administration of a dose (in mg/kg) to fasted beagle dogs of up to 310, e.g. from 60 to 310, e.g. from 140 to 310.

In another aspect the invention provides a method of increasing bioavailability or reducing variability of bioavailability levels of N-benzoylstaurosporine, said method comprising orally administering a composition of the invention to fasted beagle dogs, e.g. wherein the variability of bioavailability is less than 20%, e.g. from 5% to 17%, e.g. from 10% to 17%.

Additionally the pharmaceutical compositions of the present invention are effective with tenside materials, for example bile salts, being present in the gastro-intestinal tract. That is, the pharmaceutical compositions of the present invention are spontaneously dispersible in aqueous systems comprising such natural tensides and thus capable of providing aqueous microemulsion or aqueous micellar systems in situ which are stable. The function of the pharmaceutical compositions in the present invention upon oral administration remain substantially independent of and/or unimpaired by the relative presence or absence of bile salts at any particular time or for any given individual.

In another aspect, the invention provides a process for the production of a spontaneously dispersible pharmaceutical composition as defined above, which process comprises bringing the hydrophilic component and the surfactant (and additional components if required) into intimate admixture, and adding the active agent, i.e. N-benzoyl-staurosporine. When required, the composition may be compounded into unit dosage form, for example by encapsulation into soft or hard gelatine capsules. Optionally further components or additives, in particular a hydrophilic co-component, for example ethanol, may be mixed with the two components or with or after addition of the active agent. For example, while the use of ethanol in the compositions is not essential, ethanol may provide additional benefits, for example it has been found to be of particular advantage when the compositions are to be manufactured in soft gelatine, encapsulated form. This is because storage characteristics are improved, in particular the risk of active agent precipitation following encapsulation procedures is reduced. Thus the shelf life stability may be extended by employing ethanol or some other such co-component as an additional ingredient of the hydrophilic component.

The utility of all the pharmaceutical compositions of the present invention may be observed in standard clinical tests in, for example, known indications of active agent dosages giving equivalent blood levels of active agent; for example using dosages in the range from 25 mg to 300 mg, preferably from 100 to 225 mg, e.g. 120 to 225 mg, e.g. 150 mg of active agent per day for a 75 kilogram mammal, e.g. an adult human, and in standard animal models. The pharmaceutical profile, e.g. increased bioavailability and reduced variability of bioavailability, of the active agent provided by the compositions may be observed in standard animal tests and in clinical trials, e.g. as described above.

In another aspect, the invention provides a method of increasing bioavailability levels or reducing variability of bioavailability levels of N-benzoylstaurosporine for patients during N-benzoylstaurosporine therapy, said method comprising orally administering a composition of the invention.

In yet another aspect, the invention provides a use of N-benzoylstaurosporine in the manufacture of a medicament suitable for oral administration and having e.g. high bioavailability levels and a reduced variability of bioavailability of N-benzoylstaurosporine.

In yet another aspect, the invention provides a use of N-benzoylstaurosporine in the manufacture of a medicament having high bioavailability levels and a reduced variability of bioavailability of N-benzoylstaurosporine.

The pharmaceutical compositions of the present invention are preferably compounded in unit dosage form, for example by filling them into orally administrable capsule shells. The capsule shells may be soft or hard gelatine capsule shells.

Where the pharmaceutical composition of the present invention is in unit dosage form, each unit dosage will suitably contain from 25 to 100 mg active agent, preferably between 25 and 75 mg of the active agent, for example 25 or 50 mg. Such unit dosage forms are suitable for administration 1 to 5 times daily depending upon the particular purpose of therapy, the component of therapy and the like. However, if desired, the pharmaceutical compositions of the present invention may be in drink solution form and may include water or any other aqueous system, to provide formulations suitable for drinking.

The pharmaceutical compositions of the present invention are particularly useful for treatment and prevention of the conditions disclosed in U.S. Pat. No. 5,093,330, the contents of which are incorporated herein by reference. Most notably, these compositions show high anti-proliferative and anti-tumor activity, as a result of Protein Kinase C (PKC) inhibition, which may be extremely useful for cancer treatment. Moreover, their highly selective and potent inhibition of PKC may lead to superior clinical outcomes for the patient (i.e. delay or suppress disease progression) with equally tolerable regimens. Potential applications include a variety of solid tumors and more specifically for example breast cancer, colon cancer, ovarian cancer and leukemia. In addition, various other indications that may be affected by PKC activity may be effectively treated by these compositions, including Multi-drug Resistance (MDR), one of the major problems in currently employed cancer chemotherapy, and inflammatory diseases in general.

Thus, in another aspect the present invention provides a method of treatment comprising administering a dispersible pharmaceutical composition according to the present invention to a subject in need of such treatment.

Following is a description by way of example only of compositions of this invention and are not intended to limit the scope of the present invention.

EXAMPLES 1 TO 4

Particulate measurements, including mean size measurement of dispersed particles (diameter), measured at a 90° scattering angle and a temperature 20° C., were performed using a Malvern Zetasizer 3000. The carrier was prepared by mixing the components one with another. The active agent N-benzoyl-staurosporine is then dissolved in the carrier by stirring. No phase separation or precipitation is observed for any of the described compositions 1 to 4 which are and remain clear.

TABLE 1

Composition of Formulations 1 to 4

| | | [[I]] 1 | [[II]] 2 | [[III]] 3 | [[IV]] 4 |
|---|---|---|---|---|---|
| Co-/Surfactants %(g/g) | Cremophor RH 40 | 42.750 | 66.500 | 57.000 | |
| | Solutol HS 15 | | | | 75.905 |
| | Labrafil M2125 CS | | 18.905 | | |
| Hydrophilic Component %(g/g) | PEG 400 | 25.65 | | | |
| | Propylene Glycol | | 9.500 | 4.750 | 9.500 |
| | Ethanol abs. | 9.500 | | | 9.500 |
| | Triethylcitrate | | | 4.750 | |
| Lypophilic Component %(g/g) | Corn Oil Glycerides | 17.005 | | 28.405 | |
| Other Additives %(g/g) | Tocopherol | 0.095 | 0.095 | 0.095 | 0.095 |
| Active Agent %(g/g) | | 5.000 | 5.000 | 5.000 | 5.000 |
| Total | | | 100.0 | 100.0 | 100.0 |
| Mean Particle Size (nm) | | 31.6 | 20.4 | 66.3 | 157.3 |

EXAMPLE 5

Pharmacokinetic parameters and plasma profiles of N-benmzoylstaurosporine administered in the following three formulations A, B and C (filled into hard gelatin capsules) were analyzed:

A microemulsion preconcentrate containing Cremophor and PEG,

B microemulsion preconcentrate containing Cremophor and Labrafil,

C microemulsion preconcentrate containing Solutol.

Using a two-block latin square design, two hard gelatin capsules of each formulation A, B or C containing N-benzoyl-staurosporine were deposited deeply into the throat of each of eight male Beagle dogs (3 to 5 years, 10 to 14 kg). A subsequent rinse of the throat was performed, using 20 mL of demineralized water to be swallowed. The nominal dose of 50 mg applied per animal corresponds to actual doses between 3.5 and 4.9 mg/kg body weight (see Table 2). The dogs were fasted for at least 15 h prior to administration, but had free access to tap water throughout the experiment. Around 6 h (range 6.0-6.3) after oral administration, each animal received around 350 g pellets. Blood (3 mL) was collected from the Vena cephalica into 5 mL polystyrene tubes containing Li-heparin as anticoagulant (at least 15 I.U. heparin per mL blood), at the following time points: 0 (=before) and 0.17, 0.5, 0.75, 1, 1.5, 2, 4, 6, 8, 12, 24, 30, 36, and 48 hours post dose. The heparinized blood samples were centrifuged (about 2150 g, 10 min, about 4° C.), not longer than 30 min post withdrawal, and the supernatant plasma was collected into plain polystyrene tubes colored dark brown to avoid further daylight exposure. The plasma samples were frozen and stored below −18° C. pending analysis. Concentrations of N-benzoyl-staurosporine in plasma were determined by an HPLC method with fluorescence detection.

Figure 2:
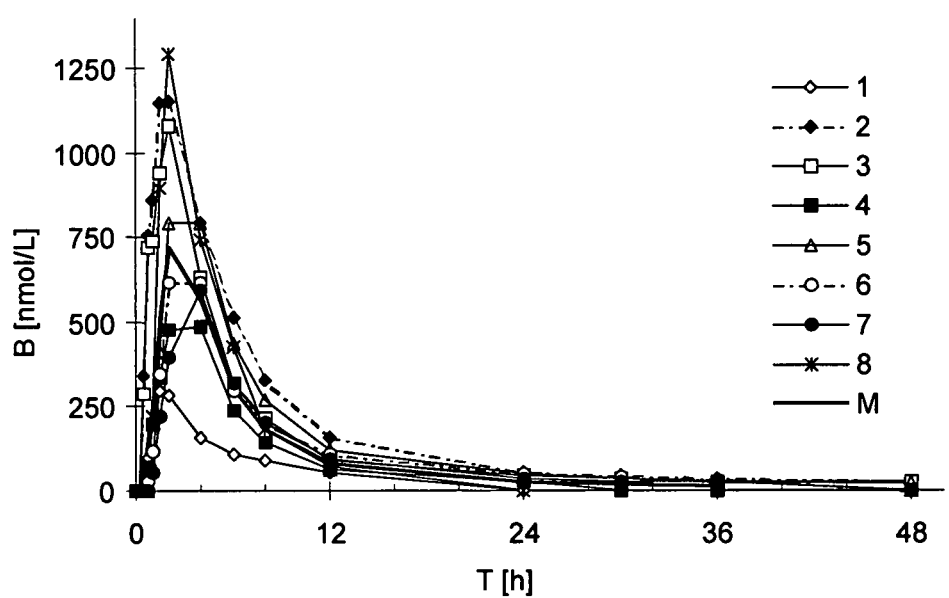
Figure 3:
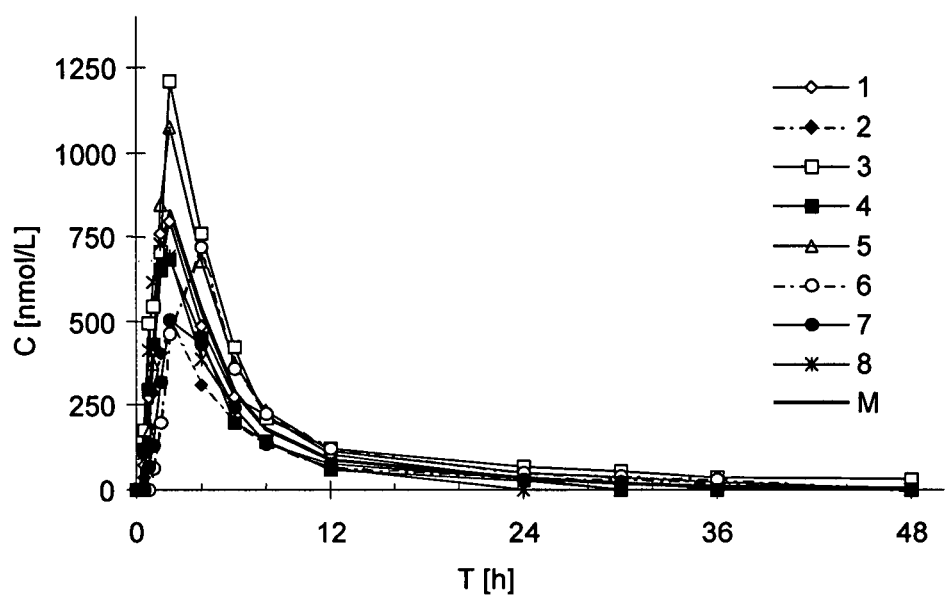

The pharmacokinetic parameters $C_{max}$ (highest observed concentration in plasma); $t_{max}$ (time to reach $C_{max}$); and AUC (0-48 h) (area under the plasma concentration-time curve from 0 to 48 h, calculated by the linear trapezoidal rule, wherein concentrations below the limit of quantitation (LOQ) were taken as 'zero'), are listed in Table 2. Individual and mean (N=6*) plasma concentrations of N-benzoyl-staurosporine in dogs 1 to 8 after oral administration of single doses of 50 mg as formulation A, B, or C are shown in FIGS. 1, 2, and 3, respectively (wherein T stands for time after dosing, and M stands for the mean concentration).

Dogs No. 2 and No. 6 were excluded from means calculation as it was questionable whether they properly ingested the appropriate dosages.

TABLE 2

Pharmacokinetic parameters
Individual and mean (N = 6*) pharmacokinetic parameters derived from the plasma concentrations of N-benzoyl-staurosporine in eight dogs after administration of single doses of 50 mg* N-benzoyl-staurosporine in form of three different formulations.

| Formulation | Parameter | Units | Animal no. 1 | 2* | 3 | 4 | 5 | 6* |
|---|---|---|---|---|---|---|---|---|
| A | Dose | mg/kg | 4.796 | 4.155 | 3.736 | 3.708 | 4.590 | 4.304 |
|   | $C_{max}$ | nmol/L | 633 | 954 | 1160 | 621 | 1148 | 816 |
|   | $C_{max}$/dose‡ | (nmol/L)/(mg/kg) | 132 | 230 | 310 | 167 | 250 | 190 |
|   | $t_{max}$ | h | 2 | 2 | 1 | 2 | 2 | 2 |
|   | AUC(0-48 h) | h · nmol/L | 4958 | 7944 | 5627 | 3565 | 7872 | 6232 |
|   | AUC(0-48 h)/dose‡ | (h · nmol/L)/(mg/kg) | 1034 | 1912 | 1506 | 961 | 1715 | 1448 |
| B | Dose | mg/kg | 4.809 | 4.157 | 3.773 | 3.847 | 4.809 | 4.379 |
|   | $C_{max}$ | nmol/L | 299 | 1153 | 1079 | 486 | 792 | 617 |
|   | $C_{max}$/dose‡ | (nmol/L)/(mg/kg) | 62 | 277 | 286 | 126 | 165 | 141 |
|   | $t_{max}$ | h | 1.5 | 2 | 2 | 4 | 2 | 2 |
|   | AUC(0-48 h) | h · nmol/L | 1840 | 8769 | 6642 | 3465 | 6496 | 5280 |
|   | AUC(0-48 h)/dose‡ | (h · nmol/L)/(mg/kg) | 383 | 2110 | 1760 | 901 | 1351 | 1206 |
| C | Dose | mg/kg | 4.733 | 4.176 | 3.883 | 3.681 | 4.897 | 4.498 |
|   | $C_{max}$ | nmol/L | 799 | 503 | 1212 | 686 | 1078 | 719 |
|   | $C_{max}$/dose‡ | (nmol/L)/(mg/kg) | 169 | 120 | 312 | 186 | 220 | 160 |
|   | $t_{max}$ | h | 2 | 2 | 2 | 2 | 2 | 4 |
|   | AUC(0-48 h) | h · nmol/L | 4890 | 3657 | 7674 | 3881 | 6528 | 5472 |
|   | AUC(0-48 h)/dose‡ | (h · nmol/L)/(mg/kg) | 1033 | 876 | 1976 | 1054 | 1333 | 1217 |

| Formulation | Parameter | Units | Animal no. 7 | 8 | Mean | SEM | [%] | N |
|---|---|---|---|---|---|---|---|---|
| A | Dose | mg/kg | 3.394 | 4.463 | 4.11 | 0.23 | 6 | 6 |
|   | $C_{max}$ | nmol/L | 633 | 924 | 853 | 106 | 12 | 6 |
|   | $C_{max}$/dose‡ | (nmol/L)/(mg/kg) | 187 | 207 | 209 | 26 | 12 | 6 |
|   | $t_{max}$ | h | 2 | 2 | 2† |   |   | 6 |
|   | AUC(0-48 h) | h · nmol/L | 3827 | 4766 | 5102 | 634 | 12 | 6 |
|   | AUC(0-48 h)/dose‡ | (h · nmol/L)/(mg/kg) | 1128 | 1068 | 1235 | 124 | 10 | 6 |
| B | Dose | mg/kg | 3.504 | 4.500 | 4.21 | 0.23 | 6 | 6 |
|   | $C_{max}$ | nmol/L | 593 | 1293 | 757 | 153 | 20 | 6 |
|   | $C_{max}$/dose‡ | (nmol/L)/(mg/kg) | 169 | 287 | 183 | 36 | 20 | 6 |
|   | $t_{max}$ | h | 4 | 2 | 2† |   |   | 6 |
|   | AUC(0-48 h) | h · nmol/L | 4531 | 5646 | 4770 | 766 | 16 | 6 |
|   | AUC(0-48 h)/dose‡ | (h · nmol/L)/(mg/kg) | 1293 | 1255 | 1157 | 191 | 17 | 6 |
| C | Dose | mg/kg | 3.550 | 4.477 | 4.20 | 0.23 | 6 | 6 |
|   | $C_{max}$ | nmol/L | 506 | 730 | 835 | 107 | 13 | 6 |
|   | $C_{max}$/dose‡ | (nmol/L)/(mg/kg) | 143 | 163 | 199 | 25 | 13 | 6 |
|   | $t_{max}$ | h | 2 | 1.5 | 2† |   |   | 6 |
|   | AUC(0-48 h) | h · nmol/L | 3671 | 3773 | 5069 | 683 | 13 | 6 |
|   | AUC(0-48 h)/dose‡ | (h · nmol/L)/(mg/kg) | 1034 | 843 | 1212 | 166 | 14 | 6 |

*either dog no. 2 got only 25 mg of B or dog no. 6 got only 25 mg of C, therefore, both were excluded from means calculation,
†median time to $C_{max}$,
‡corrected for actual dose,
SEM standard error of the mean.

The invention claimed is:

1. A pharmaceutical unit dosage which is a capsule shell containing a pharmaceutical composition comprising
   (a) 5 to 10% by weight of N-benzoyl-staurosporine;
   (b) 15 to 35% by weight of a hydrophilic component which is a polyethylene glycol of a molecular weight of 100 to 600 daltons, or a mixture of ethanol and the polyethylene glycol of a molecular weight of 100 to 600 daltons;
   (c) 30 to 55% by weight of a surfactant which is a polyoxyethylene castor oil or a mixture of a polyoxyethylene castor oil with transesterified ethoxylated vegetable oil;
   (d) 20 to 50% by weight of a lipophilic component which is a medium chain fatty acid triglyceride or corn oil glyceride; and
   (e) 0.1 to 1% by weight of an additive which is an antioxidant or an antimicrobial agent; wherein said pharmaceutical composition is suitable for oral administration and is spontaneously dispersible when diluted in an aqueous medium.

2. A pharmaceutical unit dosage form according to claim 1 having
   (a) a variability of bioavailability levels of N-benzoylstaurosporine of from 5 to 17%;
   (b) an AUC (0-48 h)/dose value (in (h·nmol/L)/(mg/kg)) of from 380 to 2000, or (c) a $C_{max}$/dose value (in (nmol/L)/(mg/kg)) of from 60 to 310, upon administration of a dose (in mg/kg) of N-benzoylstaurosporine to fasted beagle dogs.

3. A pharmaceutical unit dosage form of claim 1 wherein the hydrophilic component is a mixture of ethanol and the polyethylene glycol of a molecular weight of 100 to 600 daltons.

4. A pharmaceutical unit dosage form of claim 3 wherein the surfactant is a polyoxyethylene castor oil.

5. A pharmaceutical unit dosage form of claim 4 wherein the lipophilic component is a corn oil glyceride.

6. A pharmaceutical unit dosage form of claim 5 wherein the additive is an antioxidant.

7. A pharmaceutical unit dosage form of claim 6 wherein the antioxidant is tocopherol.

8. A pharmaceutical composition which comprises
   (a) 5 to 10% by weight of N-benzoyl-staurosporine;
   (b) 15 to 35% by weight of a hydrophilic component which is a polyethylene glycol of a molecular weight of 100 to 600 daltons, or a mixture of ethanol and the polyethylene glycol of a molecular weight of 100 to 600 daltons;
   (c) 30 to 55% by weight of a surfactant which is a polyoxyethylene castor oil or a mixture of a polyoxyethylene castor oil with transesterified ethoxylated vegetable oil;
   (d) 20 to 50% by weight of a lipophilic component which is a medium chain fatty acid triglyceride or corn oil glyceride; and
   (e) 0.1 to 1% by weight of an additive which is an antioxidant or an antimicrobial agent; wherein said pharmaceutical composition is suitable for oral administration and is spontaneously dispersible when diluted in an aqueous medium.

9. A pharmaceutical composition of claim 8 wherein the hydrophilic component is a mixture of ethanol and the polyethylene glycol of a molecular weight of 100 to 600 daltons.

10. A pharmaceutical composition of claim 9 wherein the surfactant is a polyoxyethylene castor oil.

11. A pharmaceutical unit dosage form of claim 10 wherein the lipophilic component is a corn oil glyceride.

12. A pharmaceutical unit dosage form of claim 11 wherein the additive is an antioxidant.

\* \* \* \* \*